(12) United States Patent
Bharj

(10) Patent No.: US 9,078,606 B1
(45) Date of Patent: Jul. 14, 2015

(54) SYSTEM AND METHOD FOR MEASURING BLOOD GLUCOSE IN THE HUMAN BODY WITHOUT A DRAWN BLOOD SAMPLE

(76) Inventor: Sarijit S. Bharj, Hamilton, NJ (US)

(*) Notice: Subject to any disclaimer, the term of this patent is extended or adjusted under 35 U.S.C. 154(b) by 704 days.

(21) Appl. No.: 13/204,625

(22) Filed: Aug. 5, 2011

Related U.S. Application Data

(60) Provisional application No. 61/453,121, filed on Mar. 15, 2011.

(51) Int. Cl.
- *A61B 5/00* (2006.01)
- *A61B 5/145* (2006.01)
- *A61B 5/1455* (2006.01)

(52) U.S. Cl.
CPC ........... *A61B 5/14532* (2013.01); *A61B 5/1455* (2013.01)

(58) Field of Classification Search
USPC .................................................. 600/300–365
See application file for complete search history.

(56) References Cited

U.S. PATENT DOCUMENTS

| | | | |
|---|---|---|---|
| 2,233,263 A | 2/1941 | Linder | |
| 4,011,527 A | 3/1977 | Havens | |
| 6,484,044 B1* | 11/2002 | Lilienfeld-Toal | 600/316 |
| 2002/0193673 A1* | 12/2002 | Fuller | 600/365 |
| 2005/0203358 A1* | 9/2005 | Monfre et al. | 600/331 |
| 2006/0020193 A1* | 1/2006 | Kim et al. | 600/365 |
| 2007/0297741 A1* | 12/2007 | Linder | 385/130 |
| 2008/0161725 A1* | 7/2008 | Wong et al. | 600/583 |
| 2008/0200790 A1* | 8/2008 | Kim et al. | 600/365 |
| 2008/0319293 A1* | 12/2008 | Looney et al. | 600/365 |
| 2010/0112614 A1 | 5/2010 | Axelrod et al. | |

FOREIGN PATENT DOCUMENTS

GB 1018413.3 * 11/2010

* cited by examiner

*Primary Examiner* — Michael Kahelin
*Assistant Examiner* — Mitchell E Alter
(74) *Attorney, Agent, or Firm* — LaMorte & Associates, P.C.

(57) ABSTRACT

A system and method for measuring glucose levels in a user's blood without having to draw a blood sample. A wave energy source emits wave energy. A resonance chamber is provided that receives the wave energy and produces a frequency oscillation. An opening leads into the resonance chamber that is small yet enables a significant amount of sample tissue to bulge through the opening. The sample tissue of the user is pressed against the opening. At least a portion of the sample tissue passes through the opening and into the resonance chamber. The sample tissue loads the resonance chamber and alters the frequency oscillation created by the resonance chamber. At least some of the altered frequency oscillation is indicative of blood glucose levels within the sample tissue.

15 Claims, 4 Drawing Sheets

SYSTEM AND METHOD FOR MEASURING BLOOD GLUCOSE IN THE HUMAN BODY WITHOUT A DRAWN BLOOD SAMPLE

RELATED APPLICATIONS

This application claims priority of U.S. Provisional Patent Application No. 61/453,121, entitled Microwave/Millimeter Wave Non-Invasive Glucose Meter, filed Mar. 15, 2011.

BACKGROUND OF INVENTION

1. Field of the Invention

In general, this invention relates to blood glucose measuring devices and techniques. More particularly, this invention relates to systems and methods that can measure blood glucose in the body without the need to draw a blood sample.

2. Prior Art Description

Diabetes is a chronic disease without cure. Over twenty five million people in the United States of America have diabetes. Diabetes is the seventh leading cause of death in the United States. Currently, diabetes is estimated to cost the United States health care system over one-hundred billion dollars annually.

Diabetes creates high blood glucose levels due to a deficiency of insulin production and action. This failure leads to hyperglycemia. Persistent hyperglycemia causes a variety of serious symptoms and life threatening long term complications such as dehydration, diabetic coma, cardiovascular disease, and poor blood circulation.

Many diabetics are required to take insulin in order to control the glucose levels in their blood. However, having insulin levels in the blood that are too high are just as dangerous as having insulin levels in the blood that are too low. Consequently, it is critical that diabetics who use insulin precisely monitor the level of glucose in their bodies.

The most common and accurate glucose monitoring techniques require that a blood sample be drawn from the body. This is typically done by pricking the skin with a needle or lancet to obtain a small droplet of blood. The blood is placed upon a chemically treated strip of paper. The strip of paper is then placed in a glucometer, which tests the blood and provides a glucose level reading.

Pricking the skin can be painful. Areas of the skin can also experience increased sensitively to pain if those areas are repeatedly pricked over long periods of time. Furthermore, many diabetics have blood circulation problems. As a result, these diabetics can only draw blood from certain parts of the body, such as the fingertips, where good blood flow remains. Unfortunately, the areas of the body that have good blood flow often correspond to the areas of the body that have a high concentration of nerve endings, thus increasing the pain associated with obtaining such a blood sample. The result often is that diabetics are deterred from testing and consequently test their blood glucose levels far less often than they should.

For the reasons stated above, there has been a long standing need for a glucose monitoring device that can detect the level of glucose in a diabetic without the need for a drawn a blood sample. In the prior art, certain devices have been produced that claim that they can meet this need. For instance in U.S. Patent App. Pub. No. 2010/0112614 to Axelrod, entitled Coupled Antenna Impedance Spectroscopy, a methodology is presented for measuring blood glucose levels. However, the technique does not produce accurate results in comparison to common blood drawn testing techniques. More importantly, such methodologies require the use of a spectroscope. Consequently, such testing systems are limited to use in hospitals and labs that have spectroscopes. Such testing systems cannot be made into low-cost portable devices using known technologies.

The present invention uses a small, inexpensive microwave resonance chamber to detect blood glucose levels from the tip of a diabetic's finger. Microwave resonance chambers have been in existence for over seventy-five years as is evidenced by U.S. Pat. No. 2,233,263 to Linder, entitled Resonant Cavity Oscillator. It is well known that solid-state oscillators that employ an oscillating element in a resonant cavity produce an oscillation frequency that is dependent upon the physical dimensions of the cavity. The oscillation frequency produced is so sensitive to cavity size that the oscillation frequency is affected by minute dimensional changes caused by changes in temperature. As a result, modern oscillator resonance chambers are designed to compensate for changes caused by temperature changes. See U.S. Pat. No. 4,011,527 to Havens, entitled Temperature Compensated Microwave Cavity Transistor Oscillator.

Although many designs of microwave resonance chambers exist in the prior art, no such chamber has ever been used to test for blood glucose levels.

A need therefore exists for a blood glucose meter that can be manufactured into a low-cost portable device. A need also exists for a blood glucose meter that has a monitoring accuracy that is at least as good as, or better than, the accuracy of traditional drawn blood glucose meters. These needs are met by the present invention as described and claimed below.

SUMMARY OF THE INVENTION

The present invention is a system and method for measuring glucose levels in a user's blood without having to draw a blood sample. Rather, the glucose level of the blood is tested in a non-invasive manner through the skin using energy waves in the ISM frequency bands. To test a user's blood, a wave energy source emits wave energy in either the ISM energy bands. A resonance chamber is provided that receives the wave energy and produces a frequency oscillation. An opening is provided that leads into the resonance chamber. The opening is smaller than the user's fingertip and enables a small amount of body tissue to bulge through the opening.

The fingertip or another segment of skin is pressed against the opening. At least a portion of the body tissue bulges or otherwise protrudes through the opening and into the resonance chamber. The body tissue loads the resonance chamber and alters the frequency oscillation created by the resonance chamber. At least some of the altered frequency oscillation is indicative of blood glucose levels within the body tissue.

The altered frequency oscillation is converted into a blood glucose reading. The blood glucose reading is then displayed to the user. Accordingly, using only a wave energy source, a resonance chamber and logic circuitry, an accurate non-invasive blood glucose monitor can be created that is small, lightweight, and low cost.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Figure 1:
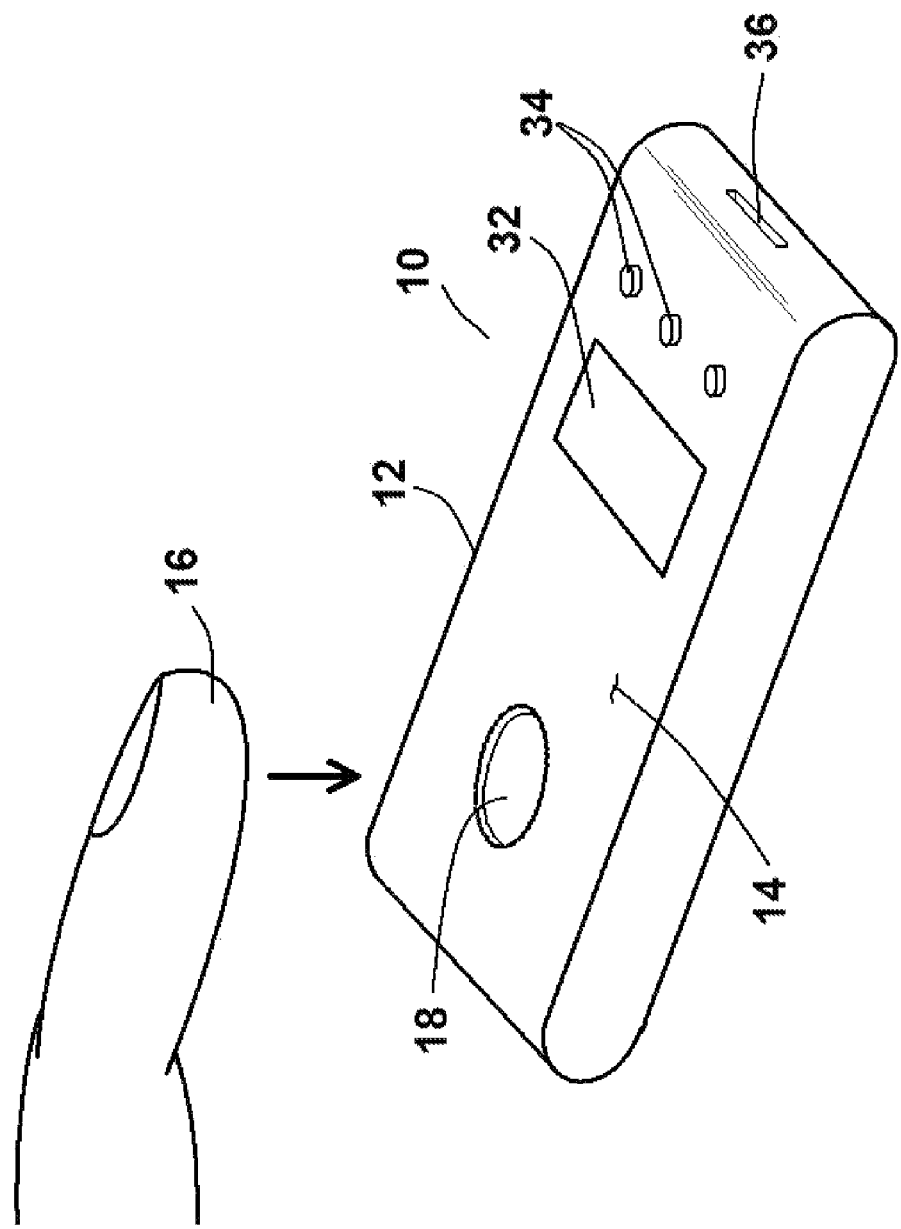
FIG. 1 shows a perspective view of an exemplary embodiment of a blood glucose monitor.
Figure 2:
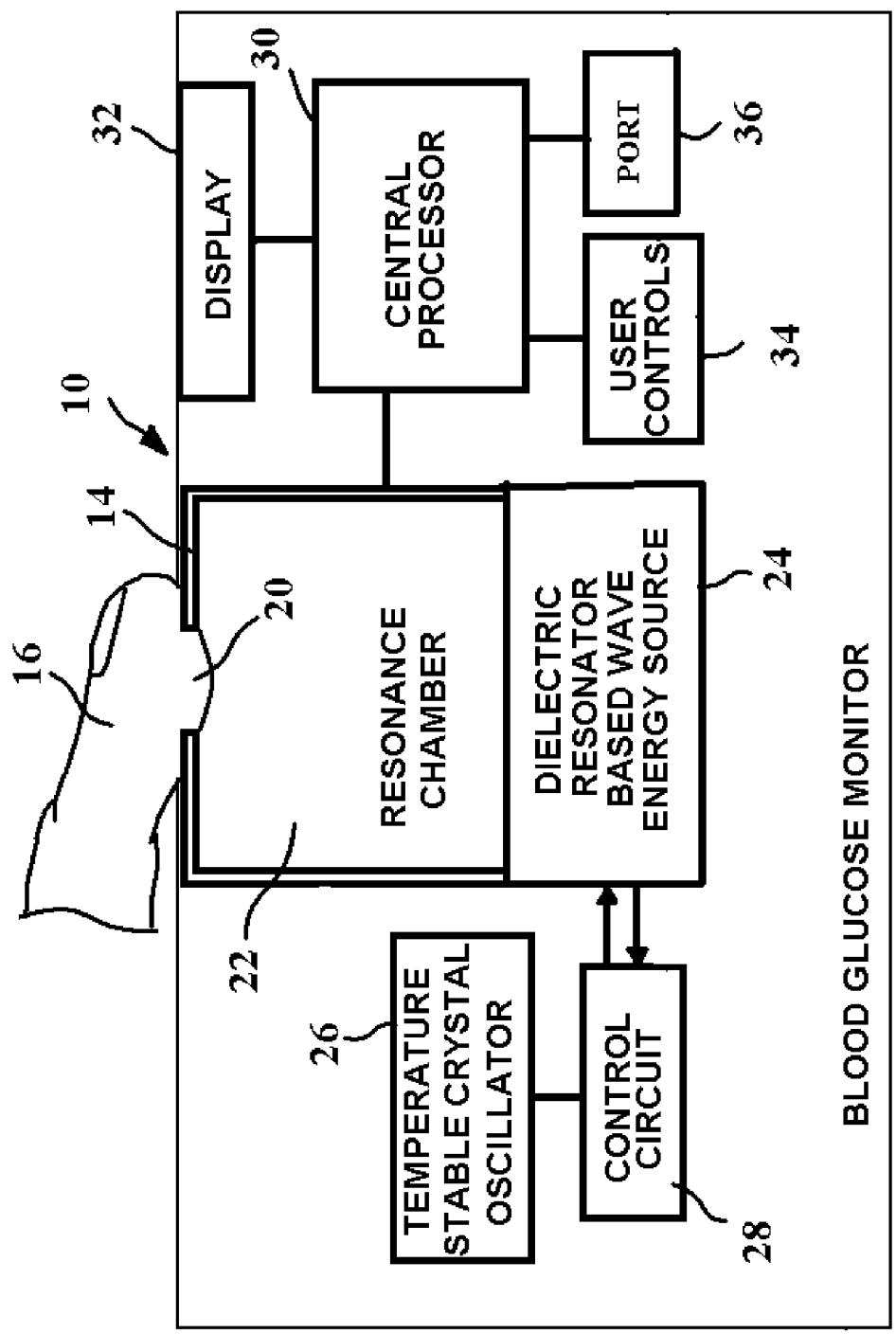
FIG. 2 is a block diagram schematic illustrating the functional components of the present invention blood glucose monitor.

Referring to FIG. 1 in conjunction with FIG. 2, a blood glucose monitor 10 is illustrated. The blood glucose monitor 10 has a housing 12. Positioned in the housing 12 is a test surface 14 upon which a person places his/her fingertip 16 or another segment of body tissue. An opening 18 is formed on the test surface 14. The opening 18 has an area of between one-half square centimeter and two square centimeters, with an area of approximately one square centimeter being preferred. In this manner, the opening 18 is smaller than the average person's fingertip. Accordingly, if a person were to place his/her fingertip 16 or another segment of body tissue over the opening 18, the body tissue would partially bulge into the opening 18, however, most of the body tissue would remain on the test surface 14.

The portion of the body tissue that bulges through the opening 18 is considered the test material for the blood glucose monitor 10. Since the majority of a person's fingertip 16 remains on the test surface 14, it will be understood that the size of a person's fingertip 16 does not matter significantly. Rather, regardless of whether the user is large or small, thin or fat, the test sample that bulges through the opening 18 remains relatively constant. Furthermore, other body tissue, such as tissue from the palm or wrist can be pressed against the opening 18. The test sample of tissue that bulges through the opening 18 remains relatively constant. The small variations that do occur because of tissue samples are compensated for through system calibrations, as will be explained. In FIG. 2, the amount of body tissue that bulges through the opening 18 is shown as sample tissue 20. The sample tissue 20 consists primarily of skin, blood, and muscle tissue. As has been previously stated, the size of the sample tissue 20 remains very consistence across a wide patient population.

The opening 18 leads into a resonance chamber 22. The dimensions of the resonance chamber 22 are fixed. A wave energy source 24 emits wave energy into the resonance chamber 22. The resonance chamber 22 produces an oscillation frequency from the wave energy that is dependent upon the bias potential and the physical characteristics of the interior of the resonance chamber 22. In the preferred embodiment, wave frequencies in the ISM (Instrument, Scientific and Medical) bands can be used. Preferably, the wave energy source 24 is a high Q factor microwave source. Such a microwave source provides a very stable (UHF) signal within environmental conditions. However, a millimeter wave (EHF) transmitter can also be used effectively.

The wave energy source 24 uses a temperature stable crystal oscillator 26 and an emission control circuit 28 to ensure that the wave energy source 24 provides a stable frequency regardless of changes in temperature, humidity, and battery strength.

The dimensions of the resonance chamber 22 are known. The resonance chamber 22 is filled mostly with air, which has a dielectric constant of one. Consequently, when nothing is placed inside the resonance chamber 22, the oscillation frequency produced by the resonance chamber 22 remains essentially constant. However, when the sample tissue 20 bulges into the resonance chamber 22, the presence of the sample tissue 20 loads the resonance chamber 22 and changes the oscillation frequency. As has been previously stated, the sample tissue 20 consists primarily of skin and blood. The skin has a fairly consistent dielectric constant that varies very little from day to day and person to person. However, it has been found that the affect of the blood on the oscillation frequency of the resonance chamber 22 is significant. The dielectric constant of the blood can vary between 30 and 74 depending upon the wave frequency being used. Of the many components contained in human blood, it has been discovered that the level of glucose contained in the blood has a significant effect on the dielectric constant attributed to that blood. Other blood chemistry elements, such as iron, tend to be constant in most individuals.

Since contributing elements to the dielectric constant of the sample tissue, such as skin and non-glucose blood chemistries, tend to be constant in any one diabetic patient, the changes in the oscillation frequency created by these elements can be considered constant background noise and can be electronically filtered. What is left is a variation in the oscillation frequency that is caused primarily by the glucose level of the blood flowing through the sample tissue 20. The changes in the oscillation frequency are significant enough to detect changes in blood glucose levels corresponding to at least one milligram per deciliter. This level of accuracy mimics that of traditional glucometers that test drawn blood samples.

The oscillation frequency of the resonance chamber 22 is detected in a traditional manner, wherein the oscillation frequency corresponds to an analog signal. The analog signal is processed by a central processing unit 30 and is converted into a voltage signal. The voltage signal is shown as a number on a display 32 of the blood glucose monitor 10. The change of frequency into voltage can be accomplished by means of digital phase lock loop, or analog phase locked loop or frequency discriminators in the control circuitry.

The central processing unit 30 is also connected to user controls 34 on the blood glucose monitor 10. The user controls 34 include an on/off control as well as input controls that enable a user to calibrate the blood glucose monitor 10 as well as initiate various preprogrammed subroutines.

An optional computer port 36 may also be coupled to the central processing unit 30. The computer port 36 allows the central processing unit 30 to download data and/or upload data from an outside computer.

The blood glucose monitor 10 is initially calibrated at the factory using blood samples from diabetic patients which are analyzed both by blood laboratories and by measurements using the blood glucose monitor 10. A calibration correlation is conducted and stored in an EEPROM or similar memory device within the control circuitry.

Figure 3:
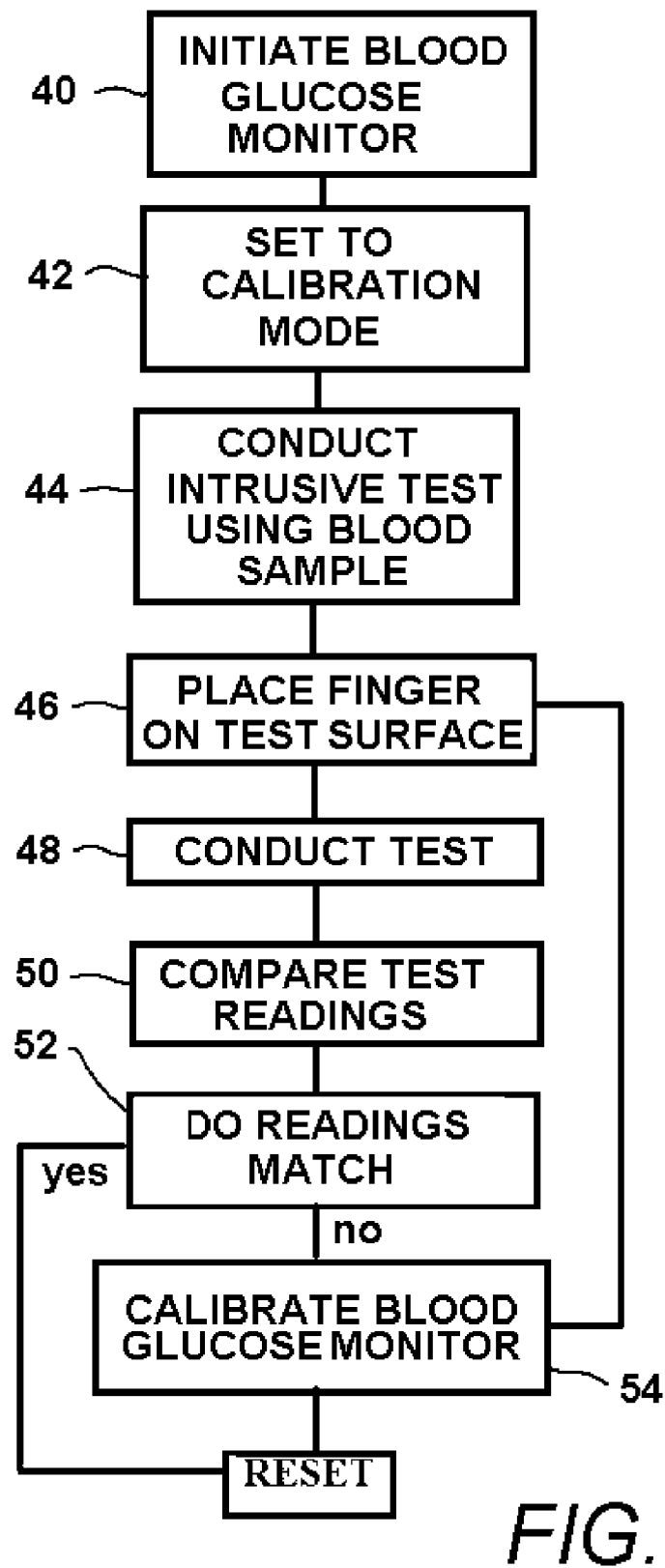
FIG. 3 is a block flow diagram illustrating the methodology of calibration for the present invention blood glucose monitor.

Referring to FIG. 3 in conjunction with FIG. 2, the method of calibrating the blood glucose monitor 10 is explained. In order to calibrate the blood glucose monitor 10, a patient initiates the blood glucose monitor 10 and sets it to calibration mode using the user inputs and the prompts on the display. See Blocks 40 and 42. A patient then draws a blood sample in the traditional manner and uses a commercially available high accuracy glucometer to obtain a blood glucose level for the blood. See Block 44. Within a predetermined time frame that is preferably less than ten seconds, a patient places his/her tissue sample over the opening 18 on the test surface 14. See Block 46. The blood glucose monitor 10 performs a test and generates a blood glucose reading. See Block 48. The readings from the blood glucose monitor 10 and the other intrusive blood sampled test are compared. See Block 50. If the reading from the blood glucose monitor 10 does not match the reading from the drawn blood, then the blood glucose monitor 10 is adjusted by the user utilizing the user controls 34. See Block 52 and Block 54. The user then removes the tissue sample from the opening 18 in the test surface 14 and resets the blood glucose monitor 10 for a new test. See Block 56. The user again performs the test. If the test results match the results of the blood drawn test, then the blood glucose monitor is properly calibrated for that user.

If the results do not match, the calibration sequence can be repeated as needed.

Calibration by cross-referencing a drawn blood test should be conducted at least once a year and perhaps as often as once a month. For users who are undergoing rapid physiological changes, such as rapid weight gain, rapid weight loss, or having just begun using a blood thinner or thickener, calibrations should be performed more often.

Figure 4:
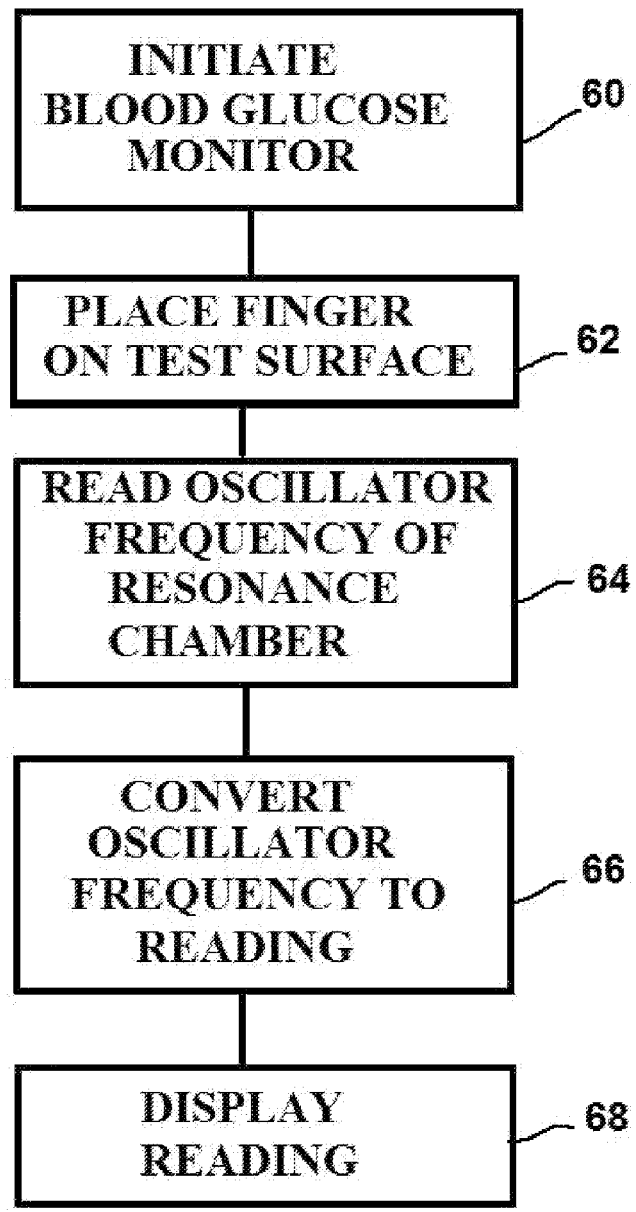
FIG. 4 is a block flow diagram illustrating the methodology of performing a test using the present invention blood glucose monitor.

Referring now to FIG. 4 in conjunction with FIG. 2, the method of operating the blood glucose monitor 10 after calibration is explained. As is indicated by Block 60, a user initiates the blood glucose monitor 10 by pressing the appropriate user control 34. Once initialized, a user places a tissue sample over the opening 18 of the test surface 14. See Block 62. The blood glucose monitor 10 automatically conducts a test by seeing how the sample tissue 20 protruding through the opening 18 affects the oscillation frequency produced by the resonance chamber 22. See Block 64. The changed oscillation frequency is converted into a numerical display signal, which is presented on the display 32. See Blocks 66 and 68. The entire test sequence should take less than ten seconds.

The glucose test monitor 10, therefore, enables users to test their blood glucose levels many times a day without having to draw blood samples. The drawing of a blood sample for calibration purposes is done seldom, giving users long periods of time to heal from the sampling. Furthermore, the blood glucose monitor 10 does not require the use of disposable and expensive lancets or blood collection strips. Consequently, the blood glucose monitor 10 does not cause the user any perpetual expenses.

It will be understood that the embodiment of the present invention that is illustrated and described is merely exemplary and that a person skilled in the art can make many variations to that embodiment. For instance, the housing shape of the blood glucose monitor is a matter of design choice. Likewise, different sized openings in the test surface can be provided for children, women, and men. All such embodiments are intended to be included within the scope of the present invention as defined by the claims.

What is claimed is:

1. A method of measuring glucose levels in a user's blood, comprising the steps of:
   providing a wave energy source that emits wave energy;
   providing a resonance chamber having an interior that receives said wave energy, therein producing a frequency oscillation;
   providing a test surface on said resonance chamber having an unobstructed opening extending therethrough that leads into said interior, wherein said opening has a first area;
   placing body tissue against said test surface over opening, wherein at least a portion of said body tissue protrudes through said opening and into said resonance chamber, wherein said portion creates an altered frequency oscillation in said resonance chamber;
   providing circuitry that converts said altered frequency oscillation into a display signal, wherein said display signal is indicative of blood glucose levels within said body tissue; and
   providing a display;
   displaying said display signal on said display.

2. The method according to claim 1, wherein said step of providing a wave energy source that emits wave energy includes providing a wave energy source that emits wave energy in bands selected from a group consisting of Instrument, Scientific and Medical (ISM) bands, microwave bands and extremely high frequency (EHF) bands.

3. The method according to claim 1, further including the step of embodying said wave energy source, said resonance chamber, said circuitry and said display in a portable handheld device.

4. The method according to claim 1, wherein said first area of said opening in said test surface is between 0.5 square centimeters and 2 square centimeters.

5. The method according to claim 1, wherein said step of providing a wave energy source includes providing a high Q microwave source.

6. A method of measuring glucose levels in a user's blood, comprising the steps of:
   providing an emission source that emits wave energy;
   providing a resonance chamber having an interior that receives said wave energy, therein causing a oscillating frequency within said resonance chamber;
   providing a test surface on said resonance chamber having an unobstructed opening extending therethrough that leads into said interior, wherein said opening has a first area;
   placing a tissue sample of the user against said test surface over said opening, wherein a portion of said tissue sample protrudes into said opening and into said resonance chamber, wherein said portion loads said resonance chamber therein creating a changed oscillating frequency within said resonance chamber that is indicative of blood glucose levels within said portion of said tissue sample;
   providing circuitry that converts said changed oscillating frequency into a display signal indicative of blood glucose level in said body tissue; and
   providing a display; and
   displaying said display signal on said display.

7. The method according to claim 6, further including the step of embodying said microwave source, said resonance chamber, said circuitry and said display in a portable handheld device.

8. The method according to claim 6, wherein said first area of said opening in said test surface is between 0.5 square centimeters and 2 square centimeters.

9. A non-invasive method for measuring blood glucose levels through a sample of body tissue, said method comprising the steps of:
   providing a resonance chamber that has an oscillating frequency in response to an energy wave input;
   providing a test surface on said resonance chamber having an unobstructed opening extending therethrough that leads into said resonance chamber, wherein said opening has a first area;
   placing the body tissue over said opening, wherein a portion of said body tissue protrudes into said opening and into said resonance chamber, therein creating a changed oscillating frequency that is indicative of blood glucose levels within said portion of said body tissue;
   providing a circuit that converts said changed oscillating frequency into a blood glucose reading; and
   displaying said blood glucose reading on a display.

10. The method according to claim 9, further including the step of embodying said resonance chamber and said circuit in a portable handheld device.

11. The method according to claim 9, wherein said first area of said opening is between 0.5 square centimeters and 2 square centimeters.

12. The method according to claim 9, wherein said energy wave input has a band selected from a group consisting of Instrument, Scientific and Medical (ISM) bands, microwave bands and extremely high frequency (EHF) bands.

13. The method according to claim 9, wherein said circuit converts said changed oscillating frequency into a voltage indicative of said blood glucose reading utilize loop circuit selected from a group consisting of a digital phase locked loop, an analog phase locked loop and frequency discriminator circuit.

14. The blood glucose apparatus for testing blood glucose levels in a tissue sample without drawing blood from said tissue sample, said apparatus comprising:

a wave energy source that emits wave energy;

a resonance chamber having an interior that receives said wave energy, therein producing a frequency oscillation, wherein a test surface is present on said resonance chamber;

an unobstructed opening formed through said test surface that leads into said interior of said resonance chamber has an opening leading to said interior, and wherein said frequency oscillation changes when said tissue sample bulges into said opening to produce a varied frequency oscillation;

circuitry that converts said varied frequency oscillation into a display signal wherein display signal is indicative of blood glucose levels within said body tissue; and a display for displaying said display signal.

15. The apparatus according to claim 13, wherein said opening on said test surface has an area between 0.5 square centimeters and 2 square centimeters.

* * * * *